United States Patent
Chen et al.

(10) Patent No.: US 11,109,747 B2
(45) Date of Patent: Sep. 7, 2021

(54) ARTHROSCOPIC SYSTEM WITH DISPOSABLE ARTHROSCOPE HAVING IMAGE ROTATION FUNCTION AND METHOD THEREOF

(71) Applicant: DYNACOLOR, INC., Taipei (TW)

(72) Inventors: Chung-Sheng Chen, Taipei (TW); Ching-Chuan Jiang, Taipei (TW); Chien-Hsiang Chang, Taipei (TW); Wei-lin Chen, Taipei (TW)

(73) Assignee: DYNACOLOR, INC., Taipei (TW)

( * ) Notice: Subject to any disclaimer, the term of this patent is extended or adjusted under 35 U.S.C. 154(b) by 273 days.

(21) Appl. No.: 16/128,541

(22) Filed: Sep. 12, 2018

(65) Prior Publication Data

US 2019/0008373 A1   Jan. 10, 2019

Related U.S. Application Data

(63) Continuation-in-part of application No. 15/432,943, filed on Feb. 15, 2017, now abandoned.

(51) Int. Cl.
| | |
|---|---|
| *A61B 1/045* | (2006.01) |
| *A61B 1/05* | (2006.01) |
| *A61B 1/317* | (2006.01) |
| *A61B 1/06* | (2006.01) |
| *A61B 1/00* | (2006.01) |
| *A61B 17/00* | (2006.01) |

(52) U.S. Cl.
CPC .......... *A61B 1/045* (2013.01); *A61B 1/00018* (2013.01); *A61B 1/00045* (2013.01); *A61B 1/00064* (2013.01); *A61B 1/00103* (2013.01); *A61B 1/00105* (2013.01); *A61B 1/05* (2013.01); *A61B 1/06* (2013.01); *A61B 1/317* (2013.01); *A61B 1/00009* (2013.01); *A61B 1/00039* (2013.01); *A61B 2017/0023* (2013.01)

(58) Field of Classification Search
CPC ......... A61B 1/05; A61B 1/045; A61B 1/0676; A61B 1/00011; A61B 1/00018; A61B 1/00009; A61B 1/00103; A61B 1/317; A61B 1/00183; A61B 1/00039
See application file for complete search history.

(56) References Cited

U.S. PATENT DOCUMENTS

| | | | | |
|---|---|---|---|---|
| 5,341,240 A | * | 8/1994 | Broome | A61B 1/055 348/65 |
| 5,519,439 A | * | 5/1996 | Keith | H04N 11/042 345/601 |
| 6,043,804 A | * | 3/2000 | Greene | G09G 5/02 345/589 |
| 2001/0015754 A1 | * | 8/2001 | Nakashima | H04N 5/232939 348/65 |

(Continued)

FOREIGN PATENT DOCUMENTS

| | | |
|---|---|---|
| CN | 100367904 C | 2/2008 |
| CN | 102341032 A | 2/2012 |

*Primary Examiner* — John P Leubecker

(57) ABSTRACT

Provided is an arthroscopic system including an disposable arthroscope having a distal end and a proximal end, and including a light source, a lens set, an image sensor, a transmitter, and a control interface. The arthroscopic system eliminates the possibility of infecting the patient with contaminated devices by its cost-effectively disposable arthroscope. Also provided is a method for image rotating in an arthroscopic system.

8 Claims, 4 Drawing Sheets

(56) References Cited

U.S. PATENT DOCUMENTS

| | | | | |
|---|---|---|---|---|
| 2005/0197536 | A1* | 9/2005 | Banik | A61B 1/0016 600/179 |
| 2006/0114986 | A1* | 6/2006 | Knapp | A61B 1/05 375/240.01 |
| 2007/0030344 | A1* | 2/2007 | Miyamoto | A61B 1/0669 348/65 |
| 2008/0108869 | A1* | 5/2008 | Sanders | A61B 1/00103 600/109 |
| 2010/0097453 | A1* | 4/2010 | Endo | H04N 7/183 348/65 |
| 2010/0228087 | A1* | 9/2010 | Shener | A61B 1/00006 600/109 |
| 2010/0261961 | A1* | 10/2010 | Scott | A61B 1/051 600/111 |
| 2011/0301414 | A1* | 12/2011 | Hotto | A61B 1/00055 600/114 |
| 2012/0220827 | A1* | 8/2012 | Sargeant | A61B 1/0052 600/109 |
| 2012/0310045 | A1* | 12/2012 | Hu | A61B 1/0051 600/110 |
| 2013/0314516 | A1* | 11/2013 | Uchihara | A61B 1/00009 348/65 |
| 2014/0114124 | A1* | 4/2014 | Dresher | A61B 1/00114 600/103 |
| 2014/0160259 | A1* | 6/2014 | Blanquart | A61B 1/00009 348/65 |
| 2014/0320621 | A1* | 10/2014 | Sonnenschein | H04N 5/2254 348/76 |
| 2014/0371535 | A1* | 12/2014 | Seto | A61B 1/0661 600/160 |
| 2015/0286867 | A1* | 10/2015 | Malesa | G06T 7/246 382/103 |
| 2016/0007833 | A1* | 1/2016 | Huang | A61B 1/0676 600/109 |
| 2016/0088999 | A1* | 3/2016 | Langell | A61B 5/7246 348/68 |
| 2016/0150943 | A1* | 6/2016 | Lin | A61B 1/045 600/109 |
| 2016/0323539 | A1* | 11/2016 | Michihata | A61B 1/00009 |
| 2016/0381263 | A1* | 12/2016 | Kang | A61B 1/00009 348/68 |
| 2017/0127924 | A1* | 5/2017 | Tsutsui | G02B 23/24 |
| 2017/0237937 | A1* | 8/2017 | Motohashi | B60R 1/00 348/148 |
| 2017/0296034 | A1* | 10/2017 | Sasaki | A61B 1/00009 |
| 2019/0125631 | A1* | 5/2019 | Allyn | A61B 5/6852 |

* cited by examiner

ARTHROSCOPIC SYSTEM WITH DISPOSABLE ARTHROSCOPE HAVING IMAGE ROTATION FUNCTION AND METHOD THEREOF

CROSS REFERENCE TO RELATED APPLICATIONS

This application is a continuation-in-part application of U.S. patent application Ser. No. 15/432,943 filed on Feb. 15, 2017, the contents of which are all hereby incorporated by reference.

FIELD OF THE INVENTION

The present application generally relates to an arthroscopic system in which image is captured, rotated and transmitted from the lens set to video display devices. More particularly, the present application relates to the arthroscopic system with the disposable arthroscope having image rotation function.

BACKGROUND OF THE INVENTION

Arthroscopy is a minimally invasive surgical procedure used to diagnose and treat a wide range of joint problems such as meniscal tears, and cartilage injury, etc. Arthroscopy allows doctors to view the joint without making a large incision through the skin and other soft tissues.

A typical arthroscopic system includes a lens set and a camera module, the lens set and the camera module are detachable. The camera module includes an image sensor, digital signal processor (DSP) and a transmitter. To display an image for doctors to operate surgery, the image sensor captures the light which is generated by a light source and reflected by the object, and converts it into digital raw data. The digital raw data is then converted into digital video data in RGB/YUV format by a digital signal processor in the camera module in serial digital interface (SDI) standard. The transmitter in the camera module then transmits the digital video data to a video captured device and then the video data is displayed on video display device for the doctor to operate surgery for patient.

Arthroscopic examination typically involves inserting an arthroscope into the patient's joint to be examined. Existing arthroscopes are typically reusable devices and must accordingly be sterilized before each use to eliminate the possibility of infecting the patient with contaminated devices. Nevertheless the possibility of infection remains if the arthroscope is not effectively or completely sterilized. Furthermore, the arthroscope may become septic in the time period between sterilization and use of the arthroscope. Therefore, the applicant has developed an arthroscopic system with a disposable arthroscope that removes the expensive digital signal processor in the disposable arthroscope, which is relatively cost-effective and decrease the risk of infection in arthroscopic surgery.

Besides, the arthroscopic system is a precision optical image system. A "viewing direction" is most important of the many factors that affect the optical properties of arthroscopes. The viewing direction refers to the direction to be observed by the arthroscope, this direction is determined by the angle of the bevel of the front end of the lens set, such as 0°, 30°, 70°, and so on. Among them, the most commonly used arthroscopic system is the 30° strabismus lens set, it can complete about 90% of arthroscopic surgery. However, the area that the arthroscopic system can observe is limited by the angle of the bevel of the lens set. When the image taking by the camera module of the arthroscopic system is skewed, the doctor needs to obtain the correct image in some ways.

The camera module and lens set in the traditional arthroscopic system are detachable. Therefore if the doctor needs to rotate the image shown on the video display device, it could be achieved by rotating the camera module. In the arthroscopic system with disposable arthroscope developed by the applicant, the camera module and the lens set are tied together, it is impossible to rotate the image shown on the video display device by rotating the camera module or the lens set. To adjust the image angle and obtain the correct image of the object, the doctor can only instruct others to assist in operating the processing system which is far away, or personally goes to the operating the processing system. Thus, the purpose of the present application to provide an arthroscopic system with disposable arthroscope, which is relatively cost-effective and does not require rotating the lens set or the image sensor set to obtain the correct image of the object on the video display device, to improve the efficiency and convenience of doctors operating arthroscopic systems.

SUMMARY OF THE INVENTION

In one aspect, the present application relates to an arthroscopic system, which comprises an disposable arthroscope having a distal end and a proximal end, and comprising a light source, a lens set, an image sensor, a transmitter, and a control interface, the light source set up to the distal end for providing a light, the lens set up to the distal end for gathering the light, the image sensor set up next to the lens set for generating digital raw data from the light, the control interface set up on the transmitter for generating a control signal, the transmitter set up between the distal end and the proximal end for transmitting the digital raw data and the control signal toward the proximal end, a processing system attached to the proximal end for capturing and converting the digital raw data into digital video data, and a video display device for displaying the digital video data. The present application eliminates the possibility of infecting the patient with contaminated devices by its cost-effectively disposable arthroscope. The present application also provides a method for image rotating in an arthroscopic system.

According to the above, the control interface is an image rotation angle control interface, and the image rotation angle can be arbitrarily selected from 1° to 360°.

According to the above, the control signal is a rotation angle control signal for controlling and indicating a rotation angle of the digital raw data.

According to the above, the processing system is a video capture and image processing system.

According to the above, the disposable arthroscope further comprises a cable.

According to the above, the transmitter is a Serializer/Deserializer (SerDes) or a low-voltage differential signaling device.

According to the above, the processing system converts digital raw data into digital video data in RGB/YUV format to be displayed by the video display device.

According to the above, the processing system comprises a digital signal processor, a central processing unit, or a computer with a graphic card.

In another aspect, the present application provides a method for image transmitting in an arthroscopic system. The method includes a light collecting step, wherein the light generated by the light source is collected by a lens set; a converting step, wherein the light collected by the lens set is converted into a digital raw data by an image sensor; a controlling step, wherein a control signal is generated by a control interface for indicate and control a rotation angle of the digital raw data; a transmitting step, wherein the digital raw data and the control signal are transmitted from a distal end of an disposable arthroscope to a proximal end of the disposable arthroscope by at least a transmitter; a signal capture, video capture and image processing step, wherein the digital raw data and the control signal are captured, and the digital raw data processed into a digital video data by a processing system; a rotating step, wherein the digital video data is digitally rotate according to the control signal by the processing system; a displaying step, wherein the rotated digital video data is displayed by a video display device.

According to the above, the control interface is an image rotation angle control interface, and the image rotation angle can be arbitrarily selected from 1° to 360°.

According to the above, the control signal is rotation angle control signal for controlling and indicating the rotation angle of the digital raw data.

According to the above, the transmitter is a Serializer/Deserializer (SerDes) or a low-voltage differential signaling device.

According to the above, the method has a use step wherein the distal end of the disposable arthroscope contacts with a patient.

According to the above, the method has a disposal step wherein the disposable arthroscope comprising light source, lens set, image sensor, control interface and transmitter is thrown away.

BRIEF DESCRIPTION OF THE DRAWINGS

This application can be better understood with reference to the following drawings and description.

DETAILED DESCRIPTION OF THE INVENTION

Figure 1:
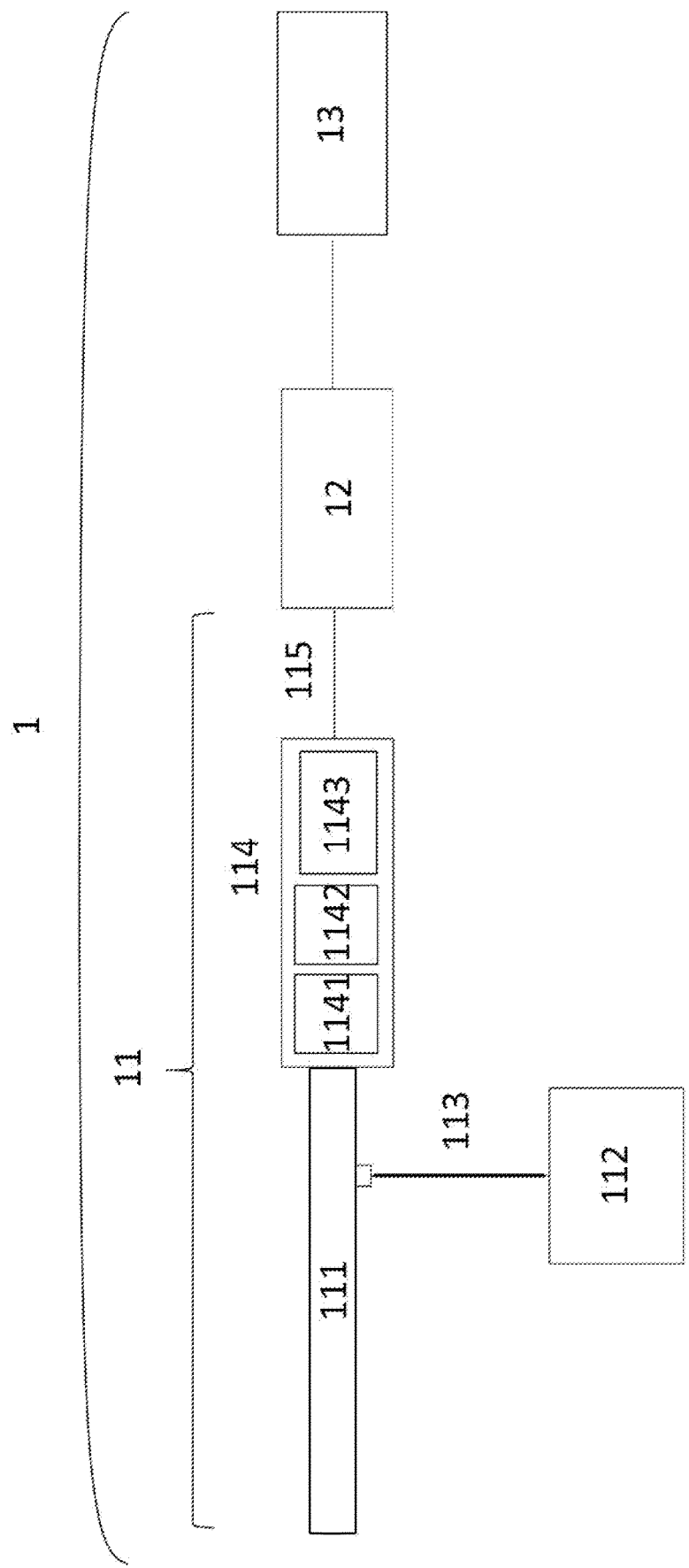
FIG. 1 presents a module chart of a typical arthroscopic system.

Referring initially to FIG. 1, a typical arthroscopic system 1 includes an arthroscope 11, a video capture device 12 and a video display device 13. The arthroscope 11 has the lens set 111, the light source 112, the light cord 113, and the camera module 114. The camera module 114 has the image sensor 1141, the digital signal processor (DSP) 1142 and the transmitter 1143. Between the transmitter 1143 and the video capture device 12, there is a cable 115. The lens set 111 and the camera module 114 are detachable.

In order to view the joint during the operation, the doctor can select the arthroscope 11 having the lens set 111 of the bevel angle at the front end. If the camera module 114 captures a skewed image, the doctor can obtain the correct image on the video display device 13 by directly rotating the camera module 114.

Figure 2:
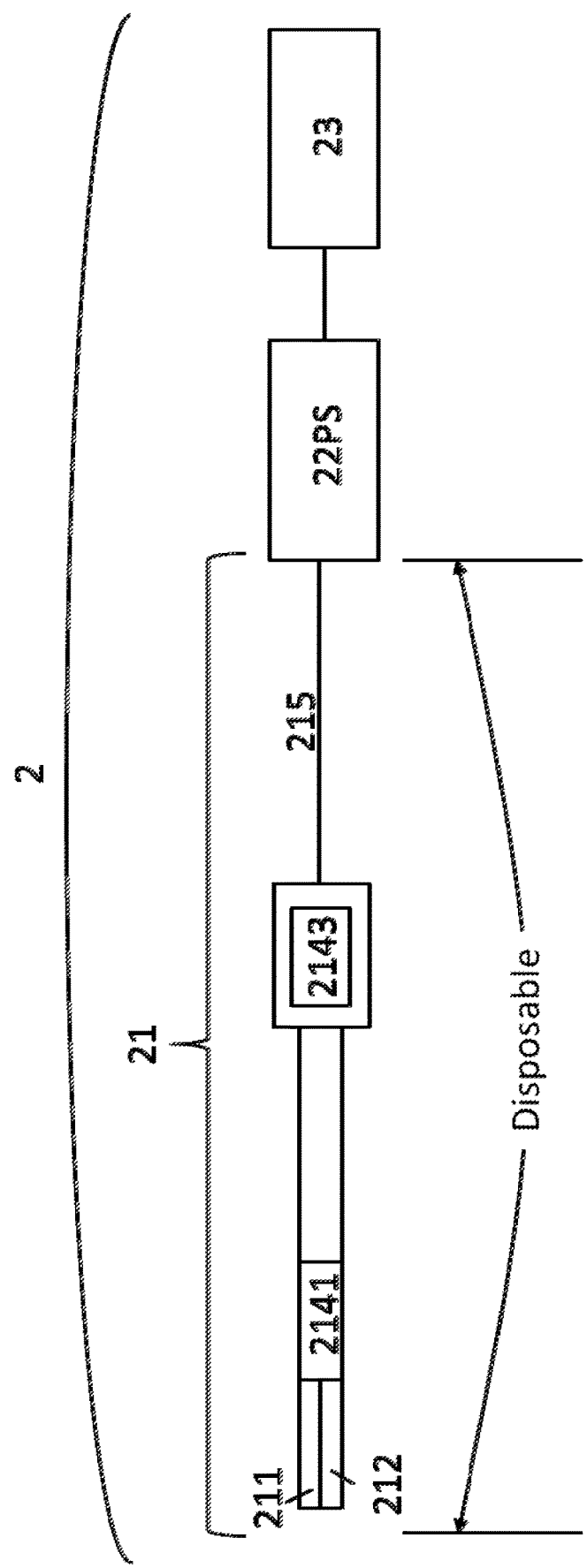
FIG. 2 presents a module chart of an arthroscopic system with disposable arthroscope.

FIG. 2 presents a module chart of an arthroscopic system 2 with disposable arthroscope. The arthroscopic system2 includes a disposable arthroscope 21, a processing system 22PS, and a video display device 23. The disposable arthroscope 21 has the lens set 211, the light source 212, the image sensor 2141, and the transmitter 2143. Between the transmitter 2143 and the processing system 22PS, there is a cable 215.

The arthroscope 21 of the arthroscopic system 2 contacts a patient to diagnose or to perform a surgery, the light source 212 conducts a light and the light is collected by lens set 211. The collected light is converted into digital raw data by an image sensor 2141, and the digital raw data is transmitted to a processing system 22PS by at least a transmitter 2143 and a cable 215. The digital raw data is captured and processed into digital video data by the processing system 22PS, and the digital video data is displayed on a video display device 23. After the diagnose or the surgery, the arthroscope 21 which contacts the patient is thrown away to avoid infection to the next patient.

However, the arthroscopic system 2 has the disadvantage that the lens set 211 and the image sensor 2141 are tied together and can't be detachable. Comparing to the arthroscopic system 1 as shown in FIG. 1, when the image show on the video display device 23 is skewed, the doctor can't obtain the correct image by rotating the lens set 211 or the image sensor 2141.

Figure 3:
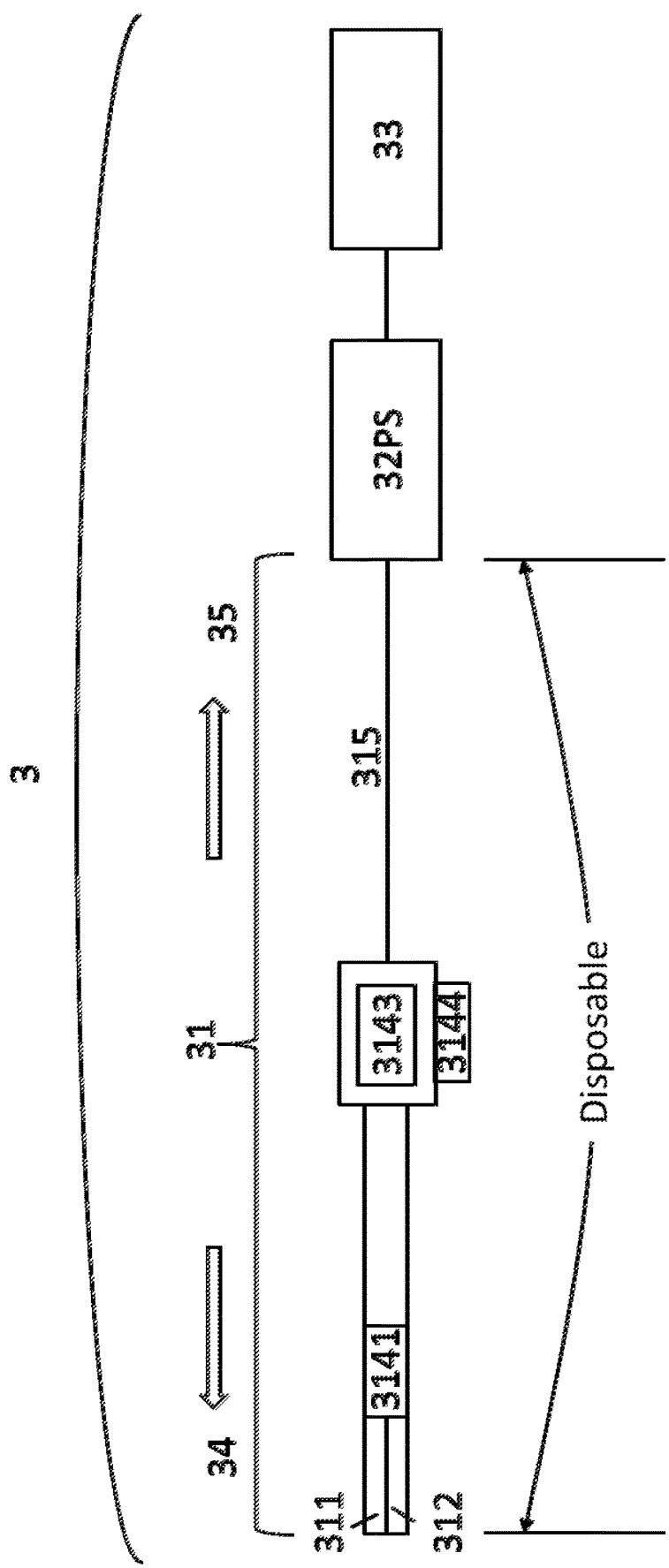
FIG. 3 presents a module chart of a novel arthroscopic system with disposable arthroscope of the present application.

FIG. 3 presents a module chart of a novel arthroscopic system with disposable arthroscope of the present application. The arthroscopic system3 having a disposable arthroscope 31, a processing system 32PS, and a video display device 33. The disposable arthroscope 31 having a distal end 34 and a proximal end 35. The present arthroscopic system 3 places the lens set 311, light source 312 and image sensor 3141 to the distal end 34 of the disposable arthroscope 31. The lens set 311 and the light source 312 are tied together and set up at the end of the distal end 34. The image sensor 3141 is set up next to the lens set 311 and the light source 312. The transmitter 3143 is set up between the distal end 34 and the proximal end 35 and next to the image sensor 3141. A control interface 3144 is set up on the transmitter 3143. Between the transmitter 3143 and the processing system 32PS, there is a cable 315 set up at the proximal end 35.

In some embodiments, the light source 312 of the present arthroscopic system includes but not limited to light-emitting diode (LED) and laser diode (LD), the image sensor 3141 includes but not limited to a Complementary Metal-Oxide-Semiconductor (CMOS), the transmitter 3143 includes but not limited to Serializer/Deserializer (SerDes) and low-voltage differential signaling (LVDS) device, and the video display device 33 includes but not limited to a screen.

The doctor can specify the rotation angle of the digital raw data through the control interface 3144 when the digital raw data generated by the image sensor 3141 has a situation of angular offset. In some embodiments, the control interface 3144 includes but not limited to one or more buttons and a knob, which can generate a control signal to control the rotation angle of the digital raw data, and the control signal may be any rotation angle such as 1° to 360°.

Digital raw data generated by the image sensor 3141 and control signal generated by the control interface 3144 are directly transmitted to the processing system 32PS which is attached to the proximal end 35 of the disposable arthroscope 31 via the transmitter 3143 and a cable 315. In the embodiment as shown in FIG. 3, the processing system 32PS is in charge of signal capturing, video capturing and image processing and is composed of known components in the field to perform its features. Digital raw data is captured by the processing system 32PS to preserve raw data for future use and convert digital raw data into digital video data in RGB/YUV format to be displayed by the video display device 33. In addition, the processing system 32PS also can digitally rotate the digital video data according to the control signal to perform a rotation function.

Hence, setting the control interface 3144 on the transmitter 3143 of the disposable arthroscope 31 can enable the doctor to control the digital raw data by the control signal generated by the control interface 3144 without turning the lens set 311 or the image sensor 3141, the digital raw data is converted into digital image data through the processing system 32PS, and the digital image data is digitally processed according to the rotation angle specified by the control signal, so that the video display device 33 plays the correct image.

Figure 4:
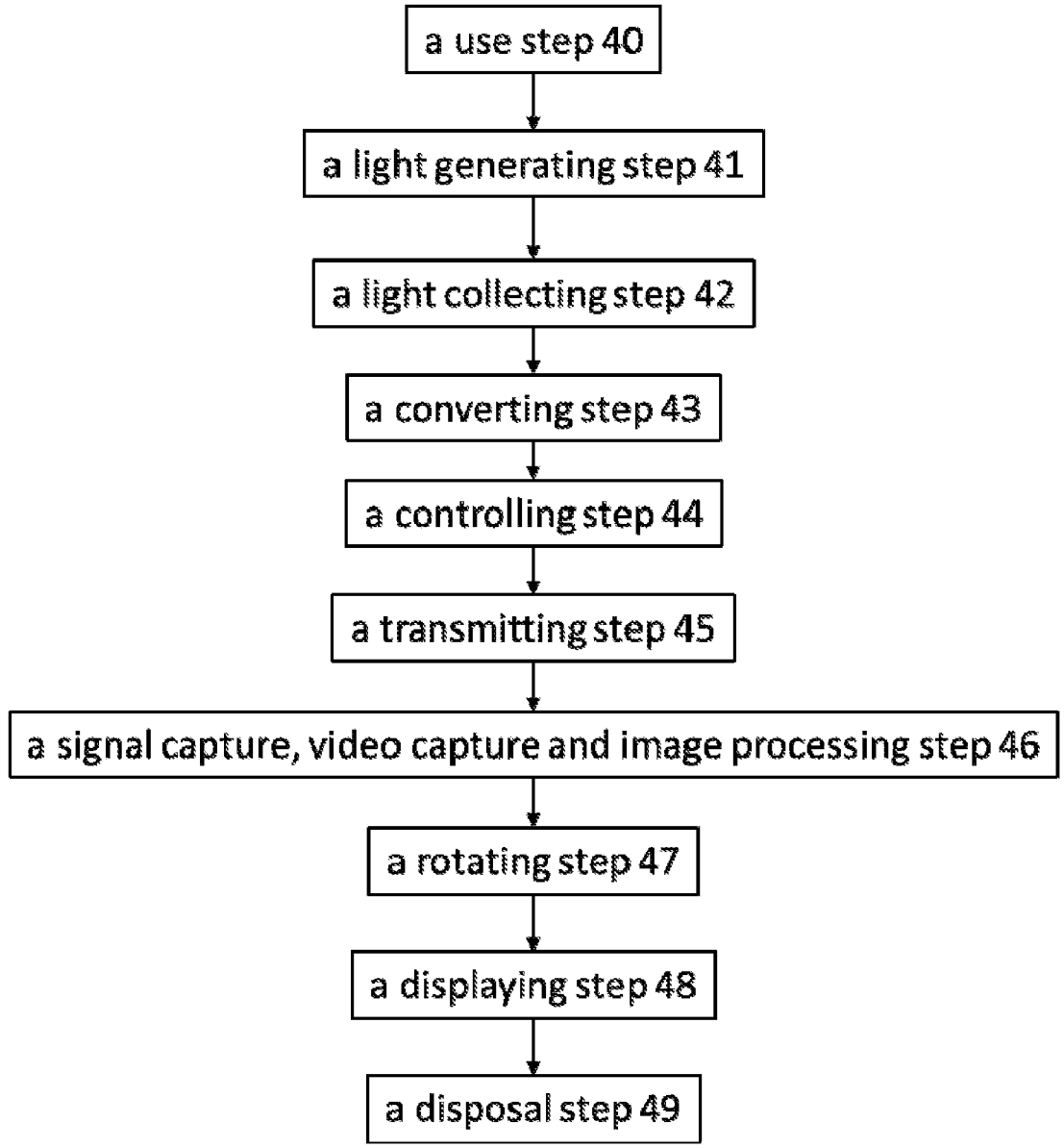
FIG. 4 presents a process flow diagram of a method for image rotating in an arthroscopic system.

Referring to FIG. 3 and FIG. 4, to apply the present application, there is a use step 40 wherein the disposable arthroscope 31 contacts a patient to diagnose or to perform a surgery. The light source 312 conducts a light generating step 41. The generated light is collected by lens set 311 in a light collecting step 42. The collected light is converted into digital raw data in a converting step 43 by an image sensor 3141. In controlling step 44, the control interface 3144 can generate a control signal to indicate and control the rotation angle of the digital raw data, and in a transmitting step 45 the digital raw data and the control signal are transmitted from a distal end 34 of an disposable arthroscope 31 to a proximal end 35 of the disposable arthroscope 31 by at least a transmitter 3143 and a cable 315. In a signal capture, video capture and image processing step 46, the digital raw data and control signal are captured, and the digital raw data processed into digital video data by the processing system 32PS. In the rotating step 47, the processing system 32PS can digitally rotate the digital video data according to the control signal. In a displaying step 48, the rotated digital video data is displayed on a video display device 33. In a disposal step 49, the disposable arthroscope 31 which contacts the patient is thrown away with the lens set 311, light source 312, image sensor 3141, transmitter 3143, the control interface 3144 and cable 315 after the diagnose or the surgery to avoid infection to the next patient.

While most of the typical arthroscopic systems apply SDI standard for transmitting data in RGB/YUV format through the arthroscope to the video capture device, the present application applies transmitter 3143 such as SerDes and LVDS device to extend the distance for transmitting digital raw data, and moves the image processing feature to the processing system 32PS. In an embodiment, the processing system 32PS conducts the image processing feature by a DSP component in the processing system 32PS. In other embodiments, the processing system 32PS conducts the image processing feature by a central processing unit or a graphic card in a computer. In some embodiments, the control interface 3144 conducts the control signal generating feature by one or more buttons and a knob, which has a lower cost. Hence, without having an expensive DSP in the arthroscope which contacts with patient during a surgery, the arthroscope in the arthroscopic system is cost-effectively disposable.

Due to the lens set and the image sensor in the disposable arthroscopic system are tied together and can't be detachable, the present application applies the control interface such as one or more buttons and knobs which are provided on the transmitter to allowing the doctor to operate the control interface (eg, touching the button with a finger) to obtain the correct image of the object by himself or herself.

Hence, the present application can enable the doctor to operate the arthroscopic system having the disposable arthroscopic conveniently and efficiency to obtain the correct image of the object when the image acquired by lens set is skewed. The present application is no need to turn the camera module of traditional arthroscopic system, it's also no need to operate the remote the processing system in arthroscopic system by the doctor or directs others to operate the processing system.

The invention claimed is:

1. An arthroscopic system comprising:
 a disposable arthroscope having a distal end and a proximal end and comprising:
  a light source set up in said distal end for providing a light;
  a lens set set up in said distal end for gathering said light, wherein said lens set has a front end with a bevel angle;
  an image sensor directly coupled to said lens set for generating a digital raw data from said light;
  a control interface set up on a transmitter between said distal end and said proximal end, wherein said control interface is configured to generate a rotation angle control signal for controlling and indicating a rotation angle of said digital raw data, and said transmitter is a Serializer/Deserializer (SerDes) configured to transmit said digital raw data and said rotation angle control signal toward said proximal end; and
  a cable set up at said proximal end for transmitting said digital raw data and said rotation angle control signal;
 a processing system attached to said proximal end for capturing and converting said digital raw data into a digital video data, wherein said digital video data is digitally rotated according to said rotation angle control signal; and
 a video display device for displaying said digital video data.

2. The arthroscopic system of claim 1, wherein said rotation angle control signal is arbitrarily selected from 1° to 360°.

3. The arthroscopic system of claim 1, wherein said processing system is a video capture and image processing system.

4. The arthroscopic system of claim 1, wherein said processing system converts said digital raw data into said digital video data in RGB/YUV format to be displayed by said video display device.

5. The arthroscopic system of claim 1, wherein said processing system comprises a digital signal processor, a central processing unit, or a computer with a graphic card.

6. A method for image rotating in the arthroscopic system of claim 1, comprising:
 a light generating step, wherein said light is generated by said light source;
 a light collecting step, wherein said light generated by said light source is collected by said lens set;
 a converting step, wherein said light collected by said lens set is converted into said digital raw data by said image sensor;
 a controlling step, wherein said rotation angle control signal is generated by said control interface for indicating and controlling a rotation angle of said digital raw data;
 a transmitting step, wherein said digital raw data and said rotation angle control signal are transmitted from said distal end of said disposable arthroscope to said proximal end of said disposable arthroscope by said transmitter, and transmitted from said proximal end of said disposable arthroscope by said cable;

a signal capture, video capture and image processing step, wherein said digital raw data and said rotation angle control signal are captured, and said digital raw data are processed into said digital video data by said processing system;

a rotating step, wherein said digital video data is digitally rotated according to said rotation angle control signal by said processing system;

a displaying step, wherein said rotated digital video data is displayed by said video display device; and a disposal step, wherein said disposable arthroscope comprising said light source, said lens set, said image sensor, said control interface, said transmitter and said cable is thrown away.

7. The method of claim 6, wherein said rotation angle control signal is arbitrarily selected from 1° to 360°.

8. The method of claim 6, further comprising a use step, wherein said distal end of said disposable arthroscope contacts with a patient.

* * * * *